United States Patent [19]

Dexter et al.

[11] 4,032,562
[45] June 28, 1977

[54] 3,5-DIALKYL-4-HYDROXYPHENYLALK-ANOIC ACID ESTERS OF POLYALKYLENE GLYCOLS

[75] Inventors: Martin Dexter, Briarcliff Manor; John D. Spivack, Spring Valley; David Herbert Steinberg, Bronx, all of N.Y.

[73] Assignee: Ciba-Geigy Corporation, Ardsley, N.Y.

[22] Filed: Oct. 24, 1975

[21] Appl. No.: 625,414

Related U.S. Application Data

[63] Continuation of Ser. No. 521,107, Nov. 5, 1974, abandoned, which is a continuation of Ser. No. 402,492, Oct. 1, 1973, abandoned, which is a continuation-in-part of Ser. No. 159,020, July 1, 1971, abandoned.

[52] U.S. Cl. .................... 260/473 S; 260/45.85 R; 260/398.5
[51] Int. Cl.² .......................................... C07C 69/76

[58] Field of Search .................... 260/473 S, 45.85

[56] References Cited

UNITED STATES PATENTS

| 3,285,855 | 11/1966 | Dexter et al. ................. 260/473 S |
| 3,441,575 | 4/1969 | Dexter et al. ................. 260/473 S |

FOREIGN PATENTS OR APPLICATIONS

| 2,231,671 | 1/1973 | Germany ........................... 260/473 |
| 7,209,214 | 1/1973 | Netherlands ..................... 260/473 |

*Primary Examiner*—Paul J. Killos
*Attorney, Agent, or Firm*—Nestor W. Shust

[57] ABSTRACT

Esters of polyalkyleneglycols with 3,5-dialkyl-4-hydroxyphenylalkanoic acids were prepared by simple esterification techniques. An example of such compounds is methoxytriethyleneglycol 3-(3',5'-di-t-butyl-4'-hydroxyphenyl)propionate. These compounds are useful as stabilizers of organic substrates subject to oxidative and thermal degradation.

4 Claims, No Drawings

3,5-DIALKYL-4-HYDROXYPHENYLALKANOIC ACID ESTERS OF POLYALKYLENE GLYCOLS

This is a continuation of application Ser. No. 521,107, filed on Nov. 5, 1974, now abandoned; which was a continuation of Ser. No. 402,492, filed on Oct. 1, 1973, now abandoned; which was a continuation in parts of Ser. No. 159,020, filed July 1, 1971, now abandoned.

DETAILED DISCLOSURE

This invention relates to 3-[3′,5′-di-t-butyl-4′-hydroxyphenyl]alkanoic acid esters of polyalkylene glycols. The esters are useful as stabilizers of organic materials which are subject to thermal and oxidative deterioration caused by heat and/or light. The novel polyalkylene glycol esters of 3-[3′,5′-di-t-butyl-4′-hydroxyphenyl]alkanoic acids of the present invention are represented by the formula

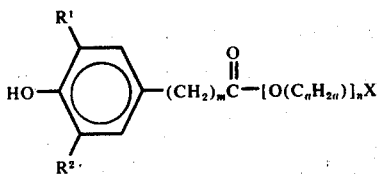

wherein each of $R^1$ and $R^2$ is a (lower)alkyl group of from one to four carbon atoms;
X is hydroxy or alkoxy containing from 1 to 2 carbon atoms; and
$a$ is an integer of from 2 to 6,
$n$ has a value of from 3 to 8,
$m$ is 1 or 2, Each of the groups $R^1$ and $R^2$ is the same or different (lower)alkyl group of from 1 to 4 carbon atoms, namely, methyl, ethyl, n-propyl, isopropyl, n-butyl, secondary-butyl, isobutyl, or tertiary butyl. The preferred groups are methyl, and tertiary butyl.

The compound of the present invention may be prepared from the appropriate 3,5-dialkyl-4-hydroxyphenylalkanoic acid, acid chloride, or (lower)alkyl esters and polyalkylene glycols using well-known esterification methods. The starting materials for preparing the compounds of this invention are commercially available and/or can be prepared according to procedures familiar to those skilled in the art.

The polyalkyleneglycols can contain two terminal hydroxy groups or an hydroxy and an alkoxy group such as methoxy or ethoxy. Examples of the polyalkylene groups are polyethylene glycol, polypropylene glycol, polybutylene glycol, polyhexylene glycol and the like. The range of $n$ is from 3 to 8.

When X in formula I is alkoxy it is preferable to react a lower alkyl ester of the alkanoic acid such as the methyl ester with the polyalkyleneglycol in the presence of a strong base such as a quanternary ammonium base, sodium methoxide and lithium hydride.

When X of Formula I is hydroxy, it is preferable to react the free propionic acid derivative with the polyalkylene glycol in the presence of a strong acid such as toluene sulfonic acid.

The esters of this invention are stabilizers of organic material normally subject to thermal and oxidative deterioration. Materials which are thus stabilized include synthetic organic polymeric substances such as vinyl resins formed from the polymerization of vinyl halides or from the copolymerization of vinyl halides with unsaturated polymerizable compounds, e.g., vinyl esters, α,β-unsaturated ketones, α,β-unsaturated aldehydes and unsaturated hydrocarbons such as butadienes and styrene; poly-α-olefins such as polyethylene, polypropylene, polybutylene, polyisoprene, and the like, including copolymers of poly-α-olefins; polyurethanes and polyamides such as polyhexamethylene adipamide and polycaprolactam; polyesters such as polyethylene terephthalates; polycarbonates; polyacetals; polystyrene; polyethyleneoxide; and copolymers such as those of high impact polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(2-ethylene-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethyleneglycol, octaethyleneglycol, dibutyleneglycol, dipropyleneglycol and the like.

These compounds are also useful for stabilizing polyamides containing polyalkyleneglycol antistatic agents.

In general, the stabilizers of this invention are employed from about 0.005% to about 10% by weight of the stabilized composition, although this will vary with the particular substrate and application. An advantageous range is from about 0.05 to about 5% and especially 0.05% to about 2%. These compounds are particularly useful for the stabilization of polyolefins such as polypropylene and polyethylene and for alkylene glycols such as triethyleneglycol.

For addition to polymeric substrates, the stabilizers can be blended before polymerization or after polymerization during the usual processing operations, for example, by hot-milling, the composition then being extruded, pressed, or the like into films, fibers, filaments, hollowspheres and the like. The heat stabilizing properties of these compounds advantageously stabilize the polymer against degradation during such processing at the high temperatures generally encountered. The stabilizers can also be dissolved in suitable solvents and sprayed on the surface of films, fabrics, filaments or the like to provide effective stabilization.

These compounds can also be used in combination with other additives such as antioxidants, sulfur-containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents demulsifiers, antifoaming agents, carbon black, accelerators, and other chemicals used in rubber compounding, plasticizers, color stabilizers, di- and tri-alkyl- and -alkylphenyl-phosphites, heat stabilizers, ultraviolet light stabilizers, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following are presented to further illustrate the present invention without introducing any limitation thereto.

EXAMPLE 1 methoxytriethylene glycol 3-(3',5'-di-t-butyl-4'-hydroxyphenyl)propionate

The aparatus was flushed with nitrogen and charged with 29.2 g of methyl 3-(3,5-di-t-butyl)-4-hydroxyphenyl)propionate, 41.1 g of methoxytriethyleneglycol and 10.2 ml of 40% methanol solution of benzyltrimethylammonium methoxide. The reaction was heated for 2½ hours between 92° and 105° C at atmospheric pressure and for an additional ½ hour at 100° C at 1 mm pressure. After cooling, the reaction mixture was neutralized with 2.4 ml of glacial acetic acid. The reaction mixture was distilled and the fraction boiling at 200°–210° C at a pressure of 1 to 3 $\mu$ was collected as the product. The refractive index of the product at 25° C was 1.5034.

Analysis for $C_{24}H_{40}O_6$: % Calculated: C, 67.89; H, 9.50; % Found: C, 68.23, H, 9.36.

In a similar fashion utilizing an equivalent amount of methyl 3-(3'-methyl-5'-t-butyl-4'-hydroxyphenyl)propionate in the above procedure in place of the designated quantity of methyl 3-(3',5'-di-t-butyl-4'-hydroxyphenyl)propionate, there is obtained methoxytriethyleneglycol 3-(3'-methyl-5'-t-butyl-4'-hydroxyphenyl)-propionate.

EXAMPLE 2

β-methoxyethyl 3-(3',5'-di-t-butyl-4'-hydroxyphenyl)propionate

The reaction flask was flushed with nitrogen and charged with 29.2 g of methyl 3-(3',5'-di-t-butyl-4'-hydroxyphenyl)propionate, 22.8 g of β-methoxyethanol and 10.2 ml of 40% methanol solution of benzyltrimethylammonium methoxide. The reaction mixture was heated under nitrogen at atmospheric pressure for approximately 1 hour at a temperature of 80°–100° C. After cooling, the reaction mixture was neutralized with 2.4 ml of glacial acetic acid. The excess of β-methoxyethanol was distilled under vacuum of 55 mm pressure at 55° C. The product was vacuum distilled and had a boiling point of 160°–165° C at 0.3 mm pressure.

Analysis for $C_{20}H_{32}O_4$: % Calculated: C, 71.39; H, 9.59; % Found: C, 71.12; H, 9.24.

In a similar fashion utilizing an equivalent amount of methyl-3(3',5'-dimethyl-4'-hydroxyphenyl)propionate in the above procedure in place of the designated quantity of methyl-3-(3',5'-di-t-butyl-4'-hydroxyphenyl)-propionate, there is obtained β-methoxyethyl 3-(3',5'-dimethyl-4'-hydroxyphenyl)propionate.

EXAMPLE 3 octaethyleneglycol 3-(3',5'-di-t-butyl-4'-hydroxyphenyl)propionate

A reaction flask was flushed with nitrogen and charged with 0.475 g of toluene sulfonic acid, 3 g of octaethyleneglycol (CARBOWAX 300), and 13.9 g of methyl 3-(3',5'-di-t-butyl-4'-hydroxyphenyl)propionate. The reaction mixture was stirred and heated at 125°–130° C for 4 hours after which it was cooled and dissolved in 500 ml of benzene, washed with water, and dried over Linde molecular sieve 4A. The reaction mixture was filtered and the benzene evaporated. The product was dissolved in 150 ml of methyl alcohol and extracted exhaustively with hexane. The methyl alcohol was stripped from the reaction product by vacuum distillation and the residue was dried at 80° C at 0.52 mm pressure.

| Analytical Results (functional group analysis for % free alcoholic OH and % hindered phenolic OH) | | | |
|---|---|---|---|
| Free Alcoholic OH | | Hindered Alcoholic OH | |
| % Calc'd | % Found | % Calc'd | % Found |
| 2.7 | 2.6 | 2.7 | 2.8 |

In a similar fashion, nonobutyleneglycol (3-methyl-5-t-butyl-4-hydroxyphenyl)acetate can be prepared by substituting an equivalent amount of nonobutyleneglycol for octaethyleneglycol and substituting an equivalent amount of methyl (3-methyl-5-t-butyl-4-hydroxyphenyl)acetate for methyl 3-(3',5'-di-t-butyl-4'-hydroxyphenyl)propionate in the above procedure.

EXAMPLE 4

Unstabilized polypropylene powder (Hercules Profax 6501) is thoroughly blended with 0.5% by weight of methoxytriethyleneglycol 3-(3',5'-di-t-butyl-4'-hydroxyphenyl)propionate. Also prepared are samples of polypropylene containing 0.1% by weight of this same stabilizer and 0.3% by weight of DSTDP (distearyl-β-thiodipropionate). The blended materials are then milled on a two-roll mill at 182° C for 10 minutes, after which time the stabilized polypropylene was sheeted from the mill and allowed to cool.

The milled polypropylene sheets are then cut into pieces and pressed for 7 minutes on a hydraulic press at 218° C, 2,000 pounds per square inch pressure. The resulting sheet of 25 mil thickness are tested for resistance to accelerated aging in a forced draft oven at 150° C.

The stabilized polypropylene with and without DSTDP is found to be more stable compared to the unstabilized composition.

Stabilized polypropylene compositions are also obtained when 0.5% of β-methoxyethyl 3-(3',5'-dimethyl-4'-hydroxyphenyl) propionate or 0.5% of methoxytriethyleneglycol 3-(3'-methyl-5'-t-butyl-4'-hydroxyphenyl)propionate are employed alone or in combination with DSTDP.

EXAMPLE 5

A water-white, refined (U.S.P. grade) mineral oil (Esso PRIMOL D) is stabilized and tested under the following test conditions.

A sample of the mineral oil (10 g) containing 0.1% by weight of methoxytriethyleneglycol 3-(3'-methyl-5'-t-butyl-4'-hydroxyphenyl)propionate is placed in a Sligh type oxidation flask filled with oxyen at room temperature (25° C) and atmospheric pressure. Thereafter, the flask is sealed to form a system having a mercury manometer which measures the pressure changes as oxygen is absorbed by the sample in the flask. The sample is then heated at 150° C until the manometer registers a decrease of 300 mm Hg pressure within the flasks with reference to the maximum pressure obtained at 150° C. Results of this test show the increase oxidation resistance for the sample containing the stabilizer.

EXAMPLE 6

High impact polystyrene resin containing elastomer (i.e., butadiene-styrene) is stabilized against loss of elongation properties by incorporation of 0.1% by weight of methoxytriethyleneglycol 3-(3',5'-di-t-butyl-4'-hydroxyphenyl) propionate. Under the test conditions described below, the stabilized resin retains a higher percentage of its original elongation properties, whereas the unstabilized resin retains less elongation properties. A substantial improvement in stability is also noted when only 0.05% of the stabilizer is employed.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch into a sheet of uniform thickness (25 mil). The sheets are then cut into strips, approximately 4 × 0.5 inches. A portion of these strips is then measured for length of elongation in the Instron Tensile tester (Instron Engineering Corporation, Quincy, Mass. The remaining portion of the strips is aged in a forced draft oven for 6 weeks at 75° C and thereafter tested for elongation. The stabilized polystyrene resin has retained its elongation property much better than the unstabilized resin.

EXAMPLE 7

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40°–45° C.

The dried rubber (25 g) is heated under nitrogen at 125° C in a Brabender mixer and to this is added with mixing 1.25 g (0.5%) of octaethyleneglycol 3(3',5'-di-t-butyl-4'-hydroxyphenyl)propionate. The composition is mixed for 5 minutes after which it is cooled and compression molded at 125° C into 5 × 5 × 0.025 inches plaques.

The plaques are placed on aluminum sheets and heated in a circulating air oven at 100° C for up to 96 hours. The viscosity of a 0.5% toluene solution of aged and unaged rubber samples are determined at 25° C. Stabilizer effectiveness is judged by the percent retention of specific viscosity, color formation and gel content after oven aging. The stabilized rubber has better viscosity, color retention, and less gel content than the rubber which is unstabilized after oven aging.

Similar results are obtained when methoxytriethylene glycol 3-(3'-methyl-5'-t-butyl-4'-hydroxyphenyl)propionate is used in place of the above mentioned stabilizer in the rubber composition.

EXAMPLE 8

To 50 g of polyacetal resin containing 0.1% of an acid scavenger, dicyandiamide, was added 0.2% by weight of various stabilizers of this invention. The resin containing these additives was milled for 7 minutes at 200° C in a Brabender Plasti-recorder. The milled formulations were subsequently pressed into a 40 mil sheet at 215° C at 350 psi for 90 seconds then cooled quickly in a cold press at 350 psi. The stabilized sheets were then remolded for 2 minutes at contact pressure and for 3 minutes at 300 psi at 215° C to give plaques 1½ × 2¼ × 125 mil. The resulting plaques were tested for resistance to accelerated aging in a force draft oven at 140° C and the time in hours to 4% loss was measured. Unstabilized samples of polyacetal containing only dicyandiamide were tested in the same manner and the results compared in Table I below.

TABLE I

| Additive(s) | Time in Hours to 4% Wt. loss at 140° C |
| --- | --- |
| methoxytriethyleneglycol 3-(3',5'-di-t-butyl-4'-hydroxyphenyl)propionate | 930 |
| β-methoxyethyl 3-(3',5'-di-t-butyl-4'-hydroxyphenyl)proprionate | 600 |
| octaethyleneglycol 3-(3',5'-di-t-butyl-4'-hydroxyphenyl)propionate | 910 |
| No Additive | 100 |

The data clearly shows the significant increase in the stabilization of the polyacetal upon addition of the antioxidant of the present invention.

EXAMPLE 9

To 50 g of Celcon polyacetal resin containing 0.1% of an acid scavenger dicyandiamide was added 0.5% by weight of the two stabilizers of this invention presented in Table II below. The resins containing these additives were milled for 7 minutes at 200° C in a Brabender Plasti-recorder. The milled formulations were subsequently pressed into a 40 mil sheet at 215° C at 350 psi for 90 seconds then cooled quickly in a cold press at 350 psi. The stabilized sheets where then remolded for 2 minutes at contact pressure and for 3 minutes at 300 psi at 215° C to give plaques 1½ × 2¼ × 125 mil. The resulting plaques were tested for resistance to accelerated aging in a force draft oven at 140° C and the time in hours to 4% weight loss was measured. The two additives of the invention methoxytriethyleneglycol 3-(3',5'-di-t-butyl-4'-hydroxyphenyl)propionate and β-methoxyethyl-3-(3',5'-di-t-butyl-4'-hydroxyphenyl)-propionate, were tested in test series designated YB and MB, respectively. In each of these designated test series samples of Celcon polyacetal containing only dicyandiamide and CAO-14, a commercial antioxidant used in polyacetals, were tested in the same manner as above. These CAO-14 samples thus serve as controls for the data comparing the additives of the invention in Table II below.

TABLE II

| Additive(s) | Test Series Designation | Time in Hours to 4% Wt. loss at 140° C |
|---|---|---|
| methoxytriethyleneglycol 3-(3',5'-di-t-butyl-4'-hydroxyphenyl)propionate | YB | 680 |
| CAO-14 | YB | 300 |
| β-methyoxyethyl 3-(3',5'-di-t-butyl-4'-hydroxyphenyl) propionate | MB | 180 |
| CAO-14 | MB | 380 |

EXAMPLE 10

A composition is prepared comprising linear polyethylene and 1.0% by weight of β-methoxyethyl 3-(3',5'-di-t-butyl-4'-hydroxyphenyl)propionate. The composition is injected molded into tensile bars which are placed in a circulating air oven at 120° C. In contrast to those molded from unstabilized linear polyethylene, tensile bars molded from the instant composition retained its tensile strength for a substantially longer period.

EXAMPLE 11

Cyclohexene, freshly distilled is stabilized by the addition thereto of 0.05% by weight of octaethyleneglycol 3-(3',5'-di-t-butyl-4'-hydroxyphenyl)propionate. The effectiveness of this stabilizer in cyclohexene is tested by the ASTM D 525-55 oxidation test. The unstabilized cyclohexene fails in shorter time as compared to the stabilized cyclohexene.

EXAMPLE 12

A stabilized high temperature lubricating oil is prepared by incorporating 2% by weight of methoxytriethyleneglycol 3-(3',5'-di-t-butyl-4'-hydroxyphenyl)propionate) to the lubricant which comprises diisoamyladipate. The stabilized composition is compared with the unstabilized lubricant by heating at 175° in the presence of air and metallic catalysts according to the test method described in Military Specification Mil-I-7808c. After 72 hours, the blank containing no stabilizer contains more sludge and has a greater viscosity than the stabilized lubricant.

EXAMPLE 13

Triethyleneglycol was stabilized to prevent acid formation by addition thereto of 0.25% by weight of various stabilizers of this invention. The samples containing these stabilizers were heated in a thermostatically controlled bath at 200° F for 120 hours. At the end of this time, the samples were cooled, and aliquots of about 1 g were removed, and accurately weighed. A known excess of standard 0.1 N potassium hydroxide was added with some phenolphthalein indicator. The excess base was determined by back-titration with a standard 0.1 N hydrochloric acid. The results are expressed as milliequivalents of acid formed per gram of sample (A) and can be calculated as follows:

$$A = \frac{N_{KOH} \times V_{KOH} - N_{HCl} \times V_{HCl}}{\text{weight of the sample}}$$

Using the above-outlined method, the following data was obtained:

| Sample | A (meg/g) |
|---|---|
| methoxytriethyleneglycol 3-(3',5'-di-t-butyl-4'-hydroxyphenyl)propionate | 1.016 |
| β-methoxyethyl 3-(3',5'-di-t-butyl-4'-hydroxyphenyl)propionate | 1.925 |
| Blank | 9.565 |

The results demonstrate that the compounds of this invention are effective in suppressing the formation of acid in triethyleneglycol when heated as opposed to samples containing no stabilizers.

What is claimed is:

1. A compound of the formula

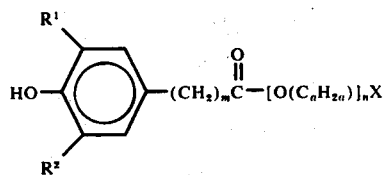

wherein each of $R^1$ and $R^2$ is a (lower) alkyl group of from one to four carbon atoms;

X is hydroxy or alkoxy containing from 1 to 2 carbon atoms; and $a$ is an integer of from 2 to 6, $n$ has a value of from 3 to 8, $m$ is 1 or 2.

2. The compound according to claim 1 wherein each of $R^1$ and $R^2$ is t-butyl or methyl.

3. The compound according to claim 2 which is methoxytriethyleneglycol 3-(3',5'=di-t-butyl-4'-hydroxyphenyl) propionate.

4. A compound according to claim 2 which is octaethyleneglycol 3-(3',5'-di-t-butyl-4'-hydroxyphenyl) propionate.

* * * * *